US012096828B2

(12) United States Patent
Dickinson et al.

(10) Patent No.: US 12,096,828 B2
(45) Date of Patent: Sep. 24, 2024

(54) WEARABLE THERMOREGULATION DEVICE, SYSTEM AND METHOD RESPONSIVE TO HOT FLASHES

(71) Applicant: Thermaband, Inc., Weston, FL (US)

(72) Inventors: Debbie A. Dickinson, Weston, FL (US); Markea C. Dickinson, Nottingham, MD (US); Harry T. Rieth, Doylestown, PA (US); Steven J. Lawson, San Pedro (BZ)

(73) Assignee: Thermaband, Inc., Weston, FL (US)

( * ) Notice: Subject to any disclaimer, the term of this patent is extended or adjusted under 35 U.S.C. 154(b) by 481 days.

(21) Appl. No.: 17/365,198

(22) Filed: Jul. 1, 2021

(65) Prior Publication Data
US 2022/0000199 A1 Jan. 6, 2022

Related U.S. Application Data

(60) Provisional application No. 63/149,564, filed on Feb. 15, 2021, provisional application No. 63/047,027, filed on Jul. 1, 2020.

(51) Int. Cl.
A44C 5/00 (2006.01)
A61B 5/00 (2006.01)
H01H 37/00 (2006.01)
H05B 1/00 (2006.01)
A61F 7/00 (2006.01)
A61F 7/02 (2006.01)
H05B 1/02 (2006.01)

(52) U.S. Cl.
CPC ............ A44C 5/0007 (2013.01); A61B 5/681 (2013.01); H01H 37/00 (2013.01); H05B 1/00 (2013.01); A61F 2007/0086 (2013.01); A61F 2007/0228 (2013.01); H01H 2203/0085 (2013.01); H05B 1/0272 (2013.01)

(58) Field of Classification Search
CPC .. A61B 5/681; A41D 20/005; A41D 2400/12; A44C 5/0007
USPC ......................................................... 700/300
See application file for complete search history.

(56) References Cited

U.S. PATENT DOCUMENTS

| 8,887,328 B2 * | 11/2014 | McKlarney | A61M 19/00 5/413 R |
| 2007/0193278 A1 * | 8/2007 | Polacek | F25B 21/02 62/3.2 |
| 2014/0200637 A1 * | 7/2014 | Larsen | A61F 7/007 607/109 |

(Continued)

FOREIGN PATENT DOCUMENTS

KR 20160118513 A * 10/2016

Primary Examiner — Chun Cao
(74) Attorney, Agent, or Firm — Prince Lobel Tye LLP

(57) ABSTRACT

A wearable thermoregulation device, system, and method. A thermoelectric device is configured to controllably heat and cool a control surface. A power source is configured to provide power to operate the thermoelectric device. A wireless communications and control module is configured to wirelessly send and receive signals, and to control the thermoelectric device. A carrier structure carries the thermoelectric device, the power source, and the wireless communications and control module, and is configured to be removably carried on the body of a user such that the heated and cooled control surface is in direct contact with the user's skin.

17 Claims, 10 Drawing Sheets

(56) References Cited

U.S. PATENT DOCUMENTS

| | | | |
|---|---|---|---|
| 2015/0094914 A1* | 4/2015 | Abreu | B60H 1/00742 |
| | | | 701/1 |
| 2015/0320588 A1* | 11/2015 | Connor | F24F 11/0001 |
| | | | 607/104 |
| 2016/0228291 A1* | 8/2016 | Calliser | A61F 7/007 |
| 2017/0266035 A1* | 9/2017 | Kuo | G08C 17/02 |
| 2017/0333667 A1* | 11/2017 | Tucker | A61B 5/0205 |
| 2018/0147086 A1* | 5/2018 | Evans | A61F 7/02 |
| 2020/0050248 A1* | 2/2020 | Smith | A61F 7/00 |
| 2020/0147380 A1* | 5/2020 | Kim | A61N 1/36021 |
| 2021/0315731 A9* | 10/2021 | Smith | G06F 1/163 |

* cited by examiner

WEARABLE THERMOREGULATION DEVICE, SYSTEM AND METHOD RESPONSIVE TO HOT FLASHES

CROSS-REFERENCE TO RELATED APPLICATIONS

This applications claims priority of Provisional Patent Application 63/047,027 filed on Jul. 1, 2020, and of Provisional Patent Application 63/149,564 filed on Feb. 15, 2021. The disclosures of both of these Provisional Patent Applications are incorporated herein by reference in their entireties and for all purposes.

BACKGROUND

This application relates to a wearable thermoregulation device.

Wearable thermoregulation devices are configured to apply one or both of cold and heat directly to the skin of a user with the aim of providing cooling or heating sensations to the user.

SUMMARY

Featured in this disclosure is a wearable thermoregulation device. In some examples the device is in the form of a wearable bracelet, although the device can take other forms that can be coupled to the user's body. In an example the wearable thermoregulation device includes a thermoelectric device that is configured to controllably heat and cool a control surface, a power source that is configured to provide power to operate the thermoelectric device, a wireless communications and control module that is configured to wirelessly send and receive signals, and to control the thermoelectric device, and a carrier structure that carries the thermoelectric device, the power source, and the wireless communications and control module, and is configured to be removably carried on the body of a user (either directly, or by being fixed to a separate device that is carried on the body such as a watch) such that the heated and cooled control surface is in direct contact with the user's skin.

In some examples the wearable thermoregulation device also includes a separate skin temperature sensor carried by the carrier structure such that it is direct contact with the user's skin at a location spaced from the thermoelectric device. The skin temperature sensor is in communication with the wireless communications and control module. In some examples the wearable thermoregulation device also includes a thermoelectric device control surface temperature sensor that is configured to determine a temperature of the thermoelectric device control surface, wherein the control surface temperature sensor is in communication with the wireless communications and control module. In some examples the wearable thermoregulation device also includes a heart rate sensor carried by the carrier structure such that it is direct contact with the user's skin, wherein the heart rate sensor is in communication with the wireless communications and control module.

In some examples the wearable thermoregulation device also includes a six-axis motion tracking device carried by the carrier structure, wherein the six-axis motion tracking device is in communication with the wireless communications and control module.

All examples and features mentioned herein can be combined in any technically possible way.

In one aspect, a wearable thermoregulation device includes a thermoelectric device that is configured to controllably heat and cool a control surface, a power source that is configured to provide power to operate the thermoelectric device, a controller, a wireless communications module that is configured to wirelessly send signals from the controller, and wirelessly receive signals, to control the thermoelectric device, and a carrier structure that carries the thermoelectric device, the power source, and the wireless communications and control module, and is configured to be removably carried on the body of a user such that the heated and cooled control surface is configured to be in direct contact with the user's skin.

Some examples include one of the above and/or below features, or any combination thereof. In some examples the wearable thermoregulation device further includes a skin temperature sensor element carried by the carrier structure such that it is configured to be in direct contact with the user's skin, wherein the skin temperature sensor element is in communication with the controller. In an example the skin temperature sensor element comprises a temperature sensor and a metal surface that is configured to touch the user's skin. In an example the skin temperature sensor element further comprises a thermally-conductive material between the temperature sensor and the metal surface. In an example the wearable thermoregulation device further includes at least one user input device. In an example the controller is responsive to both the skin temperature sensor element and the at least one user input device. In an example the controller is configured to control a cold level of the control surface based on both the sensed skin temperature and the at least one user input device.

Some examples include one of the above and/or below features, or any combination thereof. In an example the wearable thermoregulation device further includes a control surface temperature sensor that is configured to determine a temperature of the control surface, wherein the control surface temperature sensor is in communication with the controller. In an example the wearable thermoregulation device further includes a heart rate sensor carried by the carrier structure such that it is configured to be in direct contact with the user's skin, wherein the heart rate sensor is in communication with the controller. In an example the wearable thermoregulation device further includes a six-axis motion tracking device carried by the carrier structure, wherein the six-axis motion tracking device is in communication with the controller.

Some examples include one of the above and/or below features, or any combination thereof. In some examples the controller comprises firmware that is configured to detect a quick skin temperature rise and control the thermoelectric device so as to cool the control surface. In an example the firmware is further configured to smooth temperature sensor data. In an example the firmware is further configured to detect an upward inflection point in the sensed skin temperature over time. In an example the firmware is further configured to sum temperature data from a plurality of separate temperature sensors.

Some examples include one of the above and/or below features, or any combination thereof. In an example inputs to the controller include at least one of: Date/Time, Temperature sensor—wrist, Temperature sensor—device, User weighting up, User weighting down, Number of concurrent button presses up concurrent to operation, Number of concurrent button presses down concurrent to operation, Heart rate, Physical activity status, Sp02 level, Blood pressure, Skin conductivity, User sleep status, and Ambient temperature. In an example the device creates outputs that are input in a typical neural net or other machine learning technique in order to add safety dimensions to device operation. In an example the outputs comprise at least one of % current temperature of TEC, and % duration of operation of TEC.

Some examples include one of the above and/or below features, or any combination thereof. In some examples the controller is configured to implement a control algorithm. In an example the control algorithm is selected from a group of control algorithms consisting of a simple input/output map where a given discrete input is matched to a given discrete output, a more complex input/output map where button presses establish a user preference history to modify the desired output map for a given input, an even more complex input/output map where button presses form a time series user preference for a given input to further modify the desired output with respect to duration or other functionality. In an example the control algorithm is responsive to multiple inputs comprising at least biometric inputs, direct inputs from a user, implicit inputs, and contextual inputs, in order to control the thermoelectric device in accordance with the user's desires.

BRIEF DESCRIPTION OF THE DRAWINGS

Non-limiting examples illustrated in the drawings sets forth exemplary aspects of one embodiment of the wearable thermoregulation device. Various aspects of at least one example are discussed below with reference to the accompanying figures, which are not intended to be drawn to scale. The figures are included to provide illustration and a further understanding of the various aspects and examples, and are incorporated in and constitute a part of this specification, but are not intended as a definition of the limits of the inventions. In the figures, identical or nearly identical components illustrated in various figures may be represented by a like reference character or numeral. For purposes of clarity, not every component may be labeled in every figure.

DETAILED DESCRIPTION

Figure 1:
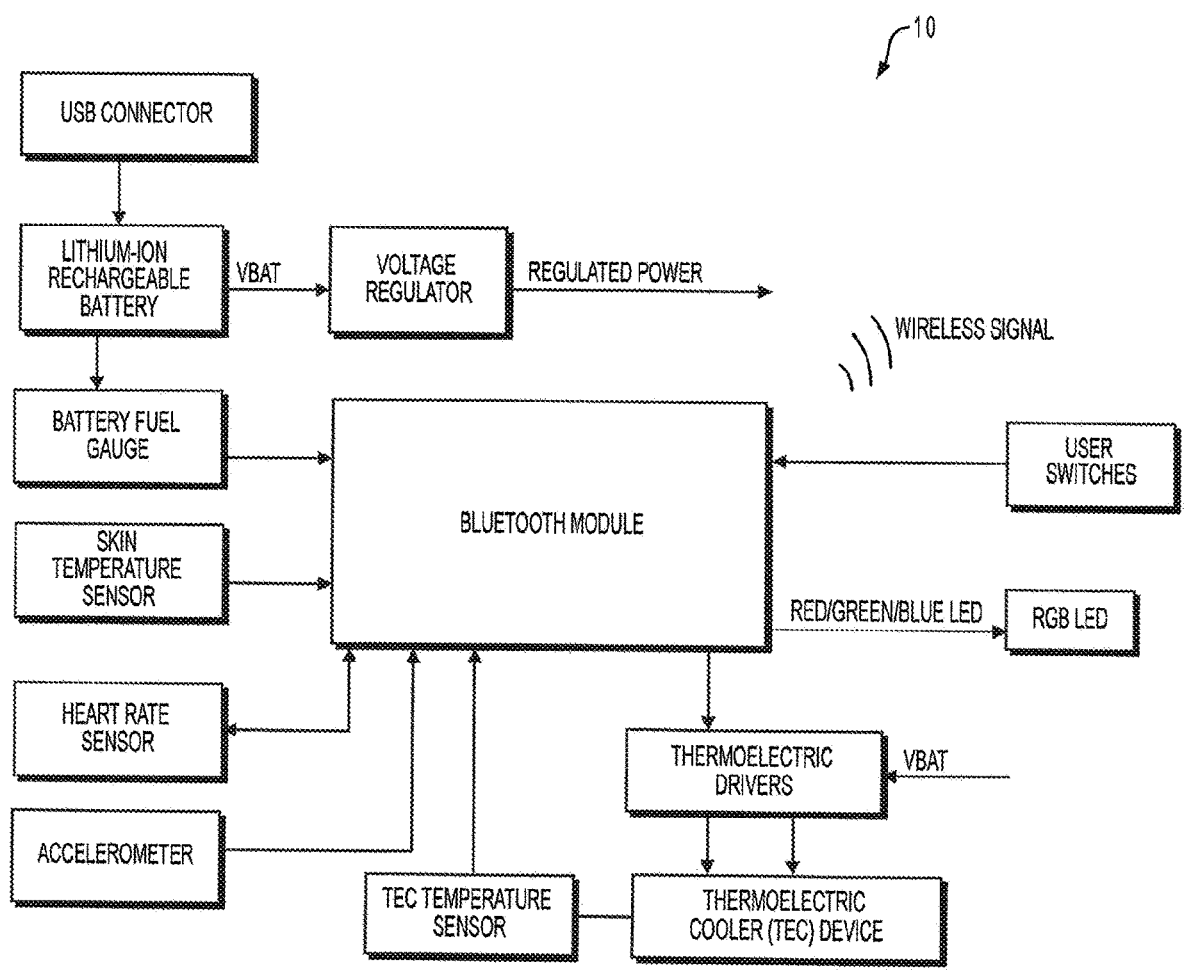
FIG. 1 is a schematic block diagram of a wearable thermoregulation device.

Examples of the methods, systems, and apparatuses discussed herein are not limited in application to the details of construction and the arrangement of components set forth in the following description or illustrated in the accompanying drawings. The methods, systems, and apparatuses are capable of implementation in other examples and of being practiced or of being carried out in various ways. Examples of specific implementations are provided herein for illustrative purposes only and are not intended to be limiting. In particular, functions, components, elements, and features discussed in connection with any one or more examples are not intended to be excluded from a similar role in any other examples.

Examples disclosed herein may be combined with other examples in any manner consistent with at least one of the principles disclosed herein, and references to "an example," "some examples," "an alternate example," "various examples," "one example" or the like are not necessarily mutually exclusive and are intended to indicate that a particular feature, structure, or characteristic described may be included in at least one example. The appearances of such terms herein are not necessarily all referring to the same example.

Also, the phraseology and terminology used herein is for the purpose of description and should not be regarded as limiting. Any references to examples, components, elements, acts, or functions of the products, systems and methods herein referred to in the singular may also embrace embodiments including a plurality, and any references in plural to any example, component, element, act, or function herein may also embrace examples including only a singularity. Accordingly, references in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Further, elements of some figures are shown and described as discrete elements in a block diagram. These may be implemented as one or more of analog circuitry or digital circuitry. Alternatively, or additionally, they may be implemented with one or more microprocessors executing software instructions. The software instructions can include digital signal processing instructions. Operations may be performed by analog circuitry or by a microprocessor executing software that performs the equivalent of the analog operation. Signal lines may be implemented as discrete analog or digital signal lines, as a discrete digital signal line with appropriate signal processing that is able to process separate signals, and/or as elements of a wireless communication system.

When processes are represented or implied in the block diagram, the steps may be performed by one element or a plurality of elements. The steps may be performed together or at different times. The elements that perform the activities may be physically the same or proximate one another, or may be physically separate. One element may perform the actions of more than one block.

Examples of the systems and methods described herein comprise computer components and computer-implemented steps that will be apparent to those skilled in the art. For example, it should be understood by one of skill in the art that the computer-implemented steps may be stored as computer-executable instructions on a computer-readable medium such as, for example, floppy disks, hard disks, optical disks, Flash ROMS, nonvolatile ROM, and RAM. Furthermore, it should be understood by one of skill in the art that the computer-executable instructions may be executed on a variety of processors such as, for example, microprocessors, digital signal processors, gate arrays, etc. For ease of exposition, not every step or element of the systems and methods described above is described herein as part of a computer system, but those skilled in the art will recognize that each step or element may have a corresponding computer system or software component. Such computer system and/or software components are therefore enabled by describing their corresponding steps or elements (that is, their functionality), and are within the scope of the disclosure.

Functions, methods, and/or components of the methods and systems disclosed herein according to various aspects and examples may be implemented or carried out in a digital signal processor (DSP) and/or other circuitry, analog or digital, suitable for performing signal processing and other functions in accord with the aspects and examples disclosed herein. Additionally or alternatively, a microprocessor, a logic controller, logic circuits, field programmable gate array(s) (FPGA), application-specific integrated circuits) (ASIC), general computing processor(s), microcontroller(s), and the like, or any combination of these, may be suitable, and may include analog or digital circuit components and/or other components with respect to any particular implementation.

Functions and components disclosed herein may operate in the digital domain, the analog domain, or a combination of the two, and certain examples include analog-to-digital converters) (ADC) and/or digital-to-analog converter(s) (DAC) where appropriate, despite the lack of illustration of ADC's or DAC's in the various figures. Further, functions and components disclosed herein may operate in a time domain, a frequency domain, or a combination of the two, and certain examples may include various forms of Fourier or similar analysis, synthesis, and/or transforms to accommodate processing in the various domains.

Any suitable hardware and/or software, including firmware and the like, may be configured to carry out or implement components of the aspects and examples disclosed herein, and various implementations of aspects and examples may include components and/or functionality in addition to those disclosed. Various implementations may include stored instructions for a digital signal processor and/or other circuitry to enable the circuitry, at least in part, to perform the functions described herein.

Following is a description, and accompanying drawings, of non-limiting examples of the wearable thermoelectric device. The following also describes thermoelectric-based temperature regulation systems and associated methods.

Overview

The following describes the major components and functionality of the electronic hardware utilized in one non-limiting example of a wearable thermoregulation device 10, as illustrated in FIG. 1. This block diagram represents a configuration of a wrist-wearable thermoregulation device. The device may alternatively be worn on other areas of the body, including, but not limited to the chest, waist or neck. Variations of this design/block diagram can also be adapted for various other configurations of the device and are discussed elsewhere in this document.

Component Description

Bluetooth Module

In one non-limiting example the device includes a certified Bluetooth module that supports Bluetooth 5 protocol, which allows for fast wireless data transfers. This module contains all the processing power for the application and for the Bluetooth wireless communication. In other words, the Bluetooth module includes a processor/controller as described herein. It has an integrated antenna, so no external antenna is required for communication with a mobile application. Bluetooth is a low power industry standard for short range wireless communication usually limited to <100 feet. It is a common technology used in mobile devices and PCs. Note that other Bluetooth modules, or discrete Bluetooth components, may be used instead. A discrete processor or controller could be used as well. Further, wireless data transfer schemes now existing or developed in the future could be used instead of Bluetooth.

The Bluetooth module along with a mobile application will allow for support of Firmware Over The Air (FOTA) updates which allows for field upgrades to the embedded firmware. These upgrades may include adding various feature functions and/or algorithms to enhance the unit operation. These upgrades are easily accomplished by the end user via the wearable thermoregulation device Mobile app.

Skin Temperature Sensor

The design supports a temperature sensor that can be attached to a small stainless-steel cap which contacts the user's skin. The temperature sensor can be a thermistor type device or silicon-based sensor. In one example it is a thermistor with a fast response time. In an example the thermistor is mounted on a small stainless-steel cap with a thermally-conductive compound. Further, the temperature sensor is preferably thermally isolated from the thermoelectric device, so that it is not influenced by the heating/cooling applied to the thermoelectric device, and to keep the thermal response to changes in skin temperature as quick as possible. Isolation can be accomplished by locating the temperature sensor on the opposite side of the wrist to the cooling module/TEC. Also, depending on the thermistor used, it may not be co-located with the TEC. The purpose of this thermistor assembly is to detect variations in skin temperature, such as those that are associated with hot flashes. In one non-limiting specific example the thermistor is sampled by the firmware every second, but other faster or slower sampling rates can be used as necessary or desired. The thermistor samples can be used to look for trends in rapid skin temperature increase that could indicate the onset of a hot-flash event. This input can be analyzed to detect a hot-flash event and turn on the thermoelectric cooler to help mitigate the event. Ideally this would be accomplished before the user would even perceive that the hot flash was occurring. Such predictive cooling of the user can potentially mitigate the effects of a hot flash to the extent that the user does not feel the hot flash, or the deleterious effects of the hot flash are lessened or occur for less time than would otherwise be the case.

Figure 2:
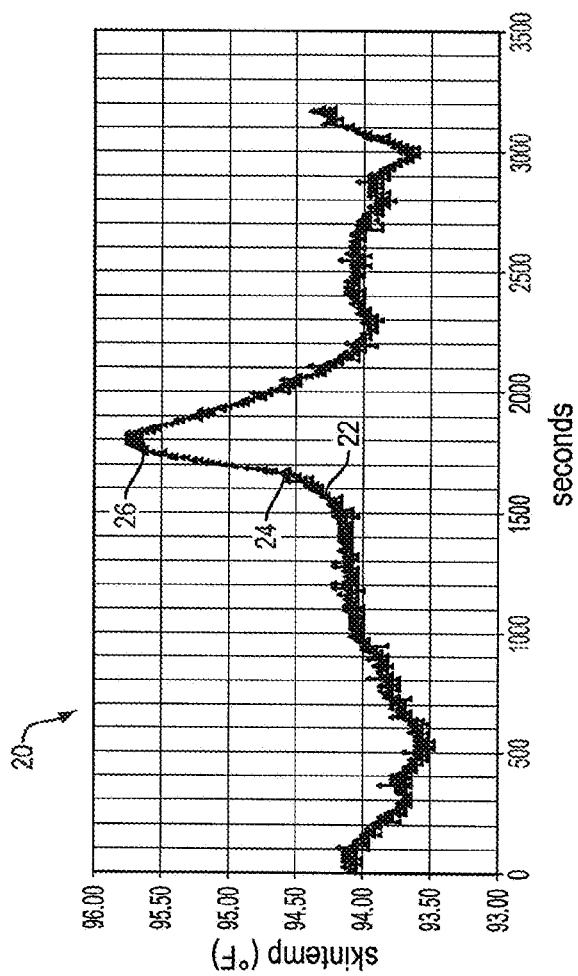
FIG. 2 is a plot of skin temperature determined by a wearable thermoregulation device vs. time, illustrating a skin temperature rise during a hot flash event.

FIG. 2 illustrates testing that shows that it was possible to detect a skin temperature rise before the user had felt the hot flash. Skin temperature data 20 illustrates rapid rise 22 (e.g., a skin temperature rise of at least about 0.5 degrees F. over about 150 seconds) before the user indication 24 of the start of a hot flash, followed by user indication 26 of the end of the hot flash. This hot flash event was recorded only at one location on the body. The wearable thermoregulation device will look for this type of rapid temperature rise related to the hot-flash event. With this system architecture it is possible to have two or more small temperature sensors remotely located on the body that could communicate with the main processing unit wirelessly via Bluetooth or other potential low power wireless technology. The potential reason for having a sensor or multiple sensors located on the body is to find the ideal location for the quickest detection of a potential hot-flash event. These remote sensors can be located on different areas of the body to form a body area network of sensors that would communicate with the processing unit on the wristband device and initiate a cooling event; this is further described below.

Thermoelectric Cooler (TEC)

The Thermoelectric Cooler is a device that has the capability to heat and cool the TEC surface by controlling the polarity of the voltage applied to the device. This phenomenon is called the Peltier effect. TEC devices are known in the field and so are not further described herein. Applying voltage to the positive side of the TEC will generate a cooling effect on the cold side by absorbing heat. The opposite side of the TEC will reject the heat, creating a hot side. When polarity is reversed to the device the effect is reversed and therefore the side contacting the skin can either cool or heat that area for a period of time.

The TEC is the primary element in the design that will create the cooling or heating event in the wearable device. One side of the TEC will make indirect contact with the skin. Typically, this indirect contact would be some type of highly thermally-conductive material. For example, a thin stainless-steel plate that make good thermal contact with the TEC and is configured to touch the skin. Cooling this plate will create a cooling sensation that will help in mitigating a hot-flash episode.

TEC Temperature Sensor

Figure 3:
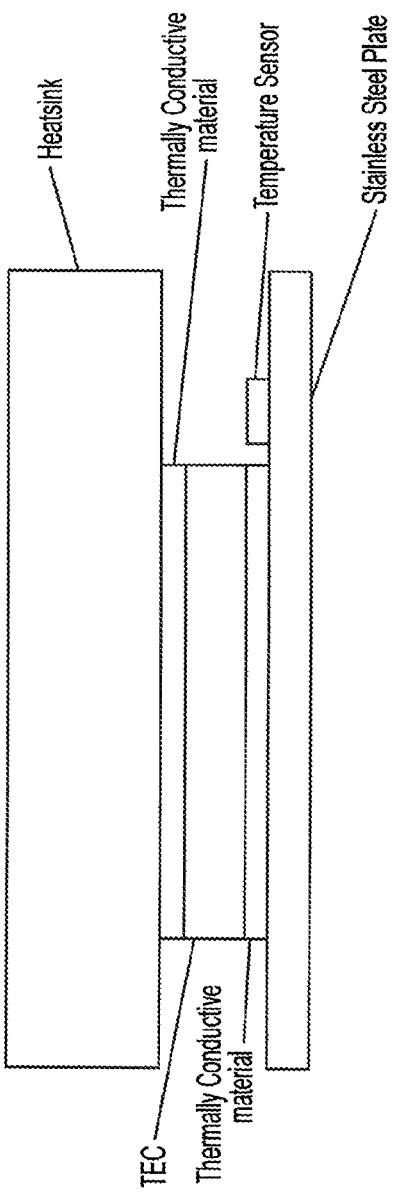
FIG. 3 is a schematic side view of a thermoelectric cooler of a wearable thermoregulation device.

The TEC temperature sensor is a temperature measuring element that will monitor the temperature of the stainless-steel plate attached to the skin side of the TEC. This temperature measuring element can be a simple thermistor or other semiconductor device. The temperature sensor is an element used in controlling the temperature on the skin side and an input to the processor in the Bluetooth module. It is part of the feedback loop that is used in a firmware algorithm that is used to monitor and regulate the TEC skin side temperature. Typical algorithms used for this type of control are PID (Proportional-Integral-Derivative) controllers. This is a control loop mechanism employing feedback (in this case the temperature sensor) to control the TEC drive. FIG. 3 illustrates how the temperature sensor could be placed near the TEC assembly stainless steel plate. The temperature sensor is also a safety feature where if for some reason there is an uncontrolled decrease/increase of temperature, the processor can turn off the supply voltage to the thermoelectric drivers thereby disconnecting power to the TEC. FIG. 3 also illustrates an arrangement of the TEC and how it can be thermally coupled to a heatsink on the non-skin side, and to a heat-conductive plate on the skin side via a thermally-conductive material such as a thermal paste of the type known in the field.

Thermoelectric Drivers

The thermoelectric driver is electronic circuitry that is used to turn power on/off to the TEC and control the polarity of the voltage to the device to generate a cooling or heating event. The thermoelectric drivers consist of semiconductor devices (MOSFETS) configured in a manner that can be controlled by the main processing unit in the BLE module. The processor will control the on and off time (duty cycle) of the TEC to control the temperature on the skin side of the stainless-steel plate.

Battery And Charger

The wearable thermoregulation device is powered by a re-chargeable Lithium-Ion Polymer battery. The battery is typically rated at 3.7 v and in this case 750 mAh. There is a battery charger that is connected to a USB connector. Charging of the battery is accomplished by connecting the wearable thermoregulation device USB port to a typical USB charger. The battery charger limits the charging rate to 500 mAh which is the typical output current of legacy USB ports/chargers. Other battery charging options like wireless charging may be added to other versions. Wireless charging would follow typical standards like Qi Compliant charging pads. Further, the device could use other battery and power-supply options.

Battery Fuel Gauge

This is a semiconductor device that gives a more accurate representation of the amount of charge on the battery. It is a better indicator than just monitoring the battery voltage. The processor will constantly monitor the fuel gauge to determine the approximate amount of operating time left for the wearable thermoregulation device before re-charging is required. The TEC is the major component that will consume most of the battery power so management of the TEC power consumption will be important in extending the battery charge.

Accelerometer/Gyroscope

The design includes a 6-axis motion tracking device of a type known in the technical field. This device includes a 3-axis gyroscope and 3-axis accelerometer. In FIG. 1 this device is labelled as "accelerometer." The device has the capability to determine activity such as step count, activity classifier (walk, run, still, sleep), orientation and tilt. This information can be passed on to the mobile app to keep track of these activities, like other fitness wearable devices. The app can keep a log of this activity to look for correlation to possible hot-flash events. For example, one might find that hot flashes occur more often during sleep and keep a log file to help predict potential hot-flash events based on a log history. This may be useful in creating algorithms that could create an automated cooling sensation that may help mitigate a hot flash event. Since the device is also monitoring skin temperature, the combination of skin temperature, motion tracking and data logging could be useful for generating algorithms to automate the application of various TEC comfort events. These aspects are further described below.

Heart Rate/Pulse Oximeter Sensor

A highly integrated pulse oximetry and heart-rate monitor module of a type known in the field is incorporated into the design. This module includes LEDs, photodetectors, optical elements, and electronics for improving the sensitivity and accuracy of these measurements. The device can function in a similar manner as other wearable fitness devices. The data gathered from this sensor will be transmitted to the mobile application to log and display the characteristics. This information can also be analyzed and used as another input in generating algorithms that can be used to provide for automated application of various TEC comfort events.

Non-Volatile Storage

The design incorporates non-volatile memory, not shown in FIG. 1. This memory is utilized to store information that is retained even when power is removed. The design incorporates a 1 Mb (128K bytes) EEPROM. This EEPROM can store various types of information like device serial #, board hardware revision, firmware revision as well as store user configuration information. The user configuration information is useful for operation when the mobile app is not available or is not needed for operation. This memory is also used to record operation function such as how often used, duration of use, time/date of use, etc. This and other information can be uploaded to the mobile application once a wireless connection is established.

User Switches

There are one or more (e.g., three) switches or other user-operable input devices such as touch sensors on the design and all three switches are easily accessible by the user and control the basic functions of the device. The switches are utilized for various functions such as power ON/OFF, cooling temperature and power cycle adjustments, and heating temperature and power cycle adjustments. The switches can be used in combinations to provide alternate functions as well like a system reset function.

For example, a user switch can be utilized to simulate a power ON/OFF function for the device. Power is never really removed from the device but rather is put into a SLEEP mode to conserve battery power. The Sleep mode simulates a power OFF condition. To wake from this SLEEP mode a user switch must be held for at least 2 seconds, at which time the processor will wake-up the unit and start normal operation. To put the unit back to SLEEP mode a user switch is pressed and held for 5 seconds, in which case the processor will do a managed shutdown and enter the SLEEP mode until the switch is pressed again.

Alternate user switch/input functions can be utilized. For example, since the device incorporates an accelerometer, user taps on the device could be detected and incorporated to emulate the switch functions descried above. For example one tap could turn on the device, two taps adjusts the temperature down, three taps adjust the temperature up, etc.

Watchdog Timer Function

The processor can incorporate a Watch Dog Timer (WDT) function. This function is a feature that allows the processor to initialize a timer that gets reset periodically by the processor. It is typically incorporated as a safety feature to recover from a potential processor failure. The WDT is set and during the processor main loop it would get reset and a new countdown would start. If for some reason the processor or firmware gets corrupted and does not execute a reset on the WDT, the WDT will expire and generate a processor reset which will bring the processor back to its initial state and restart code execution from its start point. It is an additional safety feature.

Led Indicator

There are one or two sets of RGB (Red, Green, Blue) LEDs incorporated, e.g., on a printed circuit board. These LEDs are installed to provide a visual indicator of the device status and function. Generally each RGB LED is classified as either a device status indicator or device function indicator. The processor controls the LED and can control ON and OFF times, brightness level and colors. It will be used for multiple indications events. An example of the device function indicator would be to indicate a cooling or heating event. For example, during a cooling event the blue LED can be turned on and the intensity level can be adjusted to indicate the amount of cooling. For example, if the user only wants a slight cooling event, the blue LED might be dimmer than if a stronger cooling event is desired. Conversely, if a user wants a heating event the intensity of that event could be shown by the red LED intensity. Even though with an RGB LED you can blend colors and intensity going beyond eight colors typically makes it difficult to perceive various colors. Other functions such as blinking the LED or slowly pulsing the LED can also be used in combination. An example of the device status indicator would be providing feedback of the unit status such as powered on, wireless connection achieved, low battery, battery charging, etc. Below are some examples of possible LED combinations but does not limit the possibilities.

Green LED—periodic slow pulsing with varying intensity used to indicate that the unit is ON.

Green LED—constant ON indicating that the unit has made a Bluetooth connection to the app.

RED LED—constant on when the unit is plugged into the USB port indicates battery is charging.

YELLOW LED—warning that there is an issue like low battery voltage.

BLUE LED—constant on indicating that a cooling event is in progress.

Body Area Network

In some examples the wearable thermoregulation device supports a Body Area Network (BAN). The intent of a BAN is to support multiple sensors on the body. By utilizing a Bluetooth Mesh Network it is possible to add different wearable thermoregulation devices on the body and have them communicate directly with each other.

The wearable thermoregulation device can be attached to the wrist as normal. It can work as a standalone device or communicate with another wireless device like a mobile phone, tablet or PC. Bluetooth mesh goes beyond that standard point-to-point connection of the wearable thermoregulation device to a mobile device and actually allows different sensors to be networked on the body and communicate directly to each other.

In the described example it would be possible to have remote body temperature sensors or even a remote TEC cooling device. By utilizing a secondary temperature sensor say on the chest perhaps close to the heart, one might find it detects a hot flash event sooner than might be detected on the wrist. In a BAN one can then have that temperature sensor communicate directly to the wearable thermoregulation device on the wrist to turn on the TEC to start a cooling cycle. Multiple temperature sensors could be supported at different locations on the body. Likewise, if it is desired to have a separate TEC cooling device located in another location than the wrist, it would be possible to support that function. In the example a separate TEC could be placed on the back of the neck and can be activated either by the wearable thermoregulation device, a remote temperature sensor located near on the chest, or by the mobile device app. In this type of network all the information from each sensor could be gathered and supplied to the cloud-based application.

Firmware Algorithms

There are firmware algorithms for multiple functions of the device. First, would be to detect quick temperature rise on the skin surface which would be an indicator of potential hot flash event. Second would be an algorithm to optimize the operation of the TEC. The descriptions below indicate a rough outline as to how these algorithms might work. These could be further optimized once data is collected and analyzed.

Temperature Measurements

When taking the skin temperature measurements, it may be possible to get noisy data. Without any sort of filtering algorithm this noisy data could prevent reliable event detection. To eliminate these false readings a simple averaging algorithm could be applied so that several readings would be taken at the sample rate and averaged before saving this data. For example, taking 8 or 16 readings during the sample time one could average those readings to eliminate the spike events.

Hot-Flash Detection

Figure 4:
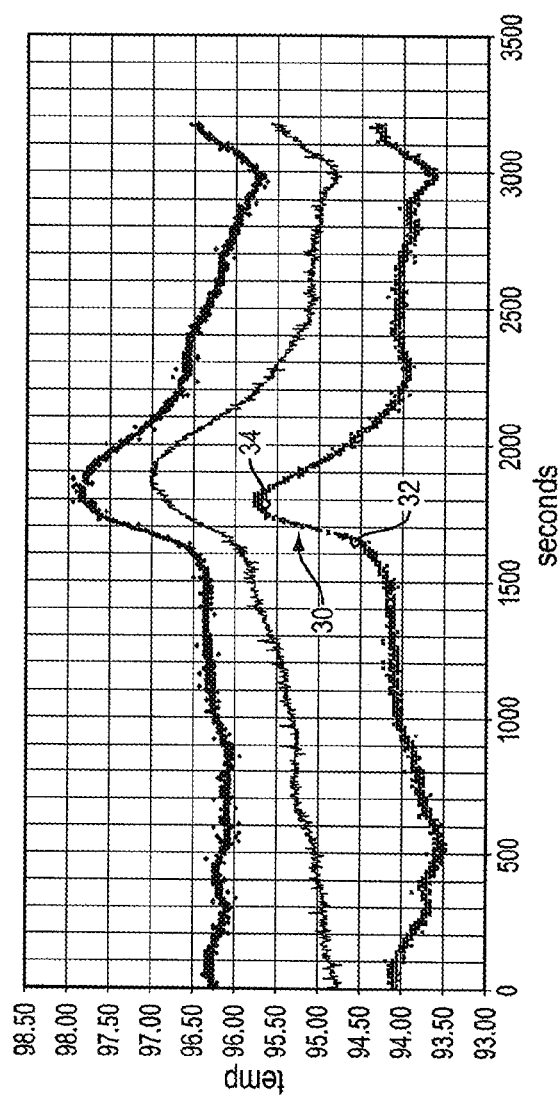
FIG. 4 is a plot of skin temperature determined by a wearable thermoregulation device vs. time, illustrating a rate of rise of a skin temperature during a hot flash event.

It is possible to detect a hot-flash event before it is detected by the subject. By collecting data from several users, one could gather enough data to help in generating an algorithm. Temperature readings would be taken at a desired sample rate. These sample readings would be evaluated to look for a quick temperature rise over a short period of time. There would need to be some noise cancellation algorithm to eliminate any erroneous readings as described previously. When there is an accelerometer in the design it may be possible to utilize this as another indicator of activity that may contribute to a hot flash. FIG. 4 illustrates a detected hot flash event 30. The bars or circles 32 and 34 indicate the beginning of a noticeable event and the end of a noticeable event.

Rate of Change Algorithm

As can be seen in FIG. 4, it is observed that there is a significant rate of skin temperature rise during a hot flash event. This temperature was measured on the arm at or close to the wrist, where a watch would typically be worn. By looking for sharp increases in temperature over a short period of time one can assume that a hot-flash event is about to occur. It can be seen in the knee of the curve that a sharp change of temperature is occurring, for example about a 0.5 degree change in about a 100 second period (e.g., about a 1 degree F. temperature increase over a period of about 150 seconds). By monitoring the rate of skin temperature change one can evaluate the onset of a hot flash event.

Simple Summing Algorithm Example

Figure 5:
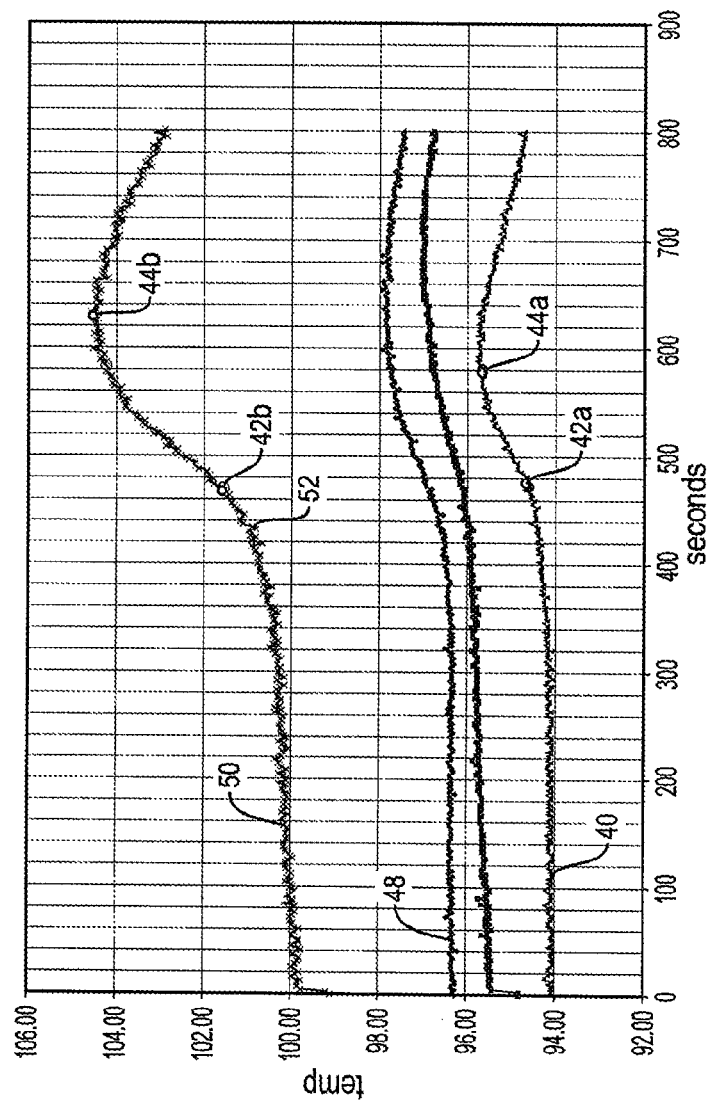
FIG. 5 is a plot of multiple skin temperatures determined by multiple wearable thermoregulation devices vs. time, illustrating a skin temperature rise during a hot flash event and an effect of a summing algorithm.

FIG. 5 presents data collected from three temperature sensors located on different parts of the body (e.g., the wrist, chest, and neck), curves 40, 46, and 48. The first circle 42a on temperature curve 40 indicates the first button push of the user indicating a hot flash detected. The second circle 44a indicates a second button push of the user indicating that the user felt the end of the hot flash event. Curves 46 and 48 also exhibit temperature rises around the hot flash event. When using a simple summing algorithm for curves 40, 46, and 48 (top curve 50 in FIG. 5), the beginning of the hot flash event (the knee or inflection point 52 of the curve) is more easily detected and occurs before first button push 42b. Second button push 44b is indicated. In FIG. 5 one may compare one thermistor detection event vs. the summing of multiple thermistors. In the lower event curve there is an about 0.5-degree skin temperature rise about 50 seconds before the detected hot flash event. In the top curve, which represents the summing algorithm, the knee of the curve is enhanced, leading to a more pronounced curve wherein a 0.5-degree skin temperature rise over about 40 seconds before the event is evident. FIG. 5 thus illustrates in summed curve 50, a sharp temperature rise 52 that is detected by the device before the first button push 42b. Summing can thus be used to automatically turn on the cooling function before the user feels the onset of a hot flash. This can make the device more effective to quickly counteract the warming sensation of a hot flash. This type of algorithm can only be applied to multiple temperature sensors. Since in one example there will be a temperature sensor on the top side of the wrist (e.g., to directly detect skin temperature) and another temperature sensor on the bottom side of the wrist (e.g., to detect the temperature of the TEC output), it may be possible to utilize this type of algorithm. Additional data can be analyzed to determine if the summing algorithm is impactful. Also, in a Body Area Network where multiple skin temperature sensors might be utilized one could find more sensitive areas of the body that might further enhance the knee of the curve.

TEC Algorithms

Controlling the TEC to maintain proper cooling and heating cycles can be accomplished using a closed loop control system where the processor will monitor multiple inputs to determine the best way to control the TEC. The primary feedback is the TEC output (the TEC skin surface) temperature, effect of heatsink temperature rise, and battery power. The TEC has a heatsink side and a skin temperature side. By monitoring the TEC skin temperature during a cooling event the TEC heatsink side temperature can be inferred; this can be used to help manage the TEC driving algorithm. Testing can help to find the optimal characteristics for driving the TEC under the different user scenarios.

TEC Drivers

The TEC on and off times are controlled by the microcontroller. The TEC is generally controlled by Pulse Width Modulation (PWM) technique which is intended to optimize the target temperature on the skin surface, the rate of temperature change, duration of operation and heating effect on the heatsink side of the TEC. A general method for controlling a closed loop system is by utilizing a Proportional-Integral-Derivative (PID) controller. This method of control employs one or multiple feedback inputs that impact the control of the device, in this case the TEC Not all three control terms are necessarily required as in some cases only one or two terms might provide suitable control. Testing can be used to generate the data need for parameters for PID type control. Below are some examples scenarios.

Example 1

In this example the User Input Target parameters are defined in priority as: cool as fast as possible, cool to coldest temperature possible, cool for the longest duration possible.

The user inputs are significant in providing a control loop that can obtain these targets. Important variables are temperature and time. However, other variables might be considered, such as battery level (amount of power left in the battery to obtain desired results) and how much heat will be transferred from the heatsink side to the skin contact side. For this scenario one could generate an algorithm that turns on the TEC as hard as possible (i.e., 100% duty cycle). Turning on the TEC as hard as possible will also satisfy reaching the coldest temperature possible. However, in doing this the duration of operation will be significantly reduced as other factors like battery power consumption and heatsink temperature rise will have a major impact on duration.

By profiling the TEC design which includes the heatsink effect one can provide different weights to these inputs (control terms) for optimizing the User Input Target parameters.

Example 2

In another scenario, the User Input Target parameters are defined in priority as cool as fast as possible and cool for the longest duration possible.

The important variables are temperature and time. These may or may not be weighted differently. The other variables include Battery Level (amount of power left in the battery to obtain desired results) and how much heat will be transferred from the heatsink side to the skin contact side now carry a larger weight (control term). For this scenario one could generate an algorithm that turns on the TEC as hard as possible (100% duty cycle), to cool as fast as possible. By monitoring the TEC skin side temperature and backing off on the cooling temperature by changing TEC duty cycle will help prevent a quick temperature rise on the TEC heatsink side, thereby extending the operating duration. Monitoring the battery level will be more important now as operating duration is a key element. However, in extending the operating duration, the level of cooling will be sacrificed. So even though the device cooled quickly, the algorithm has put more weight on other terms to meet the duration weighting. By monitoring the skin temperature, the processor can determine how long the unit can run before the cooling event would turn into a heating event.

Other inputs from sensors like the accelerometer and heart-rate sensor may be added to the PID control loop based on the acquisition of more data to see what type of input/weighting would be assigned to these terms. Testing of the device and user operational profiling will help in assigning values to these control terms.

The TEC algorithms can be initiated by the user through the mobile app. Another possible input to trigger a TEC event could be the early detection of a hot-flash event in which case a profile of cooling as quick and as cold as possible for a short duration might be appropriate. Many unique profiles could be generated by the user to meet their specific needs. The profiles could be created and stored on the mobile app but can also be downloaded into the device so that operation without a connection to the mobile app is possible. Each profile would require a different weighting of control terms for the TEC algorithm.

Figure 6:
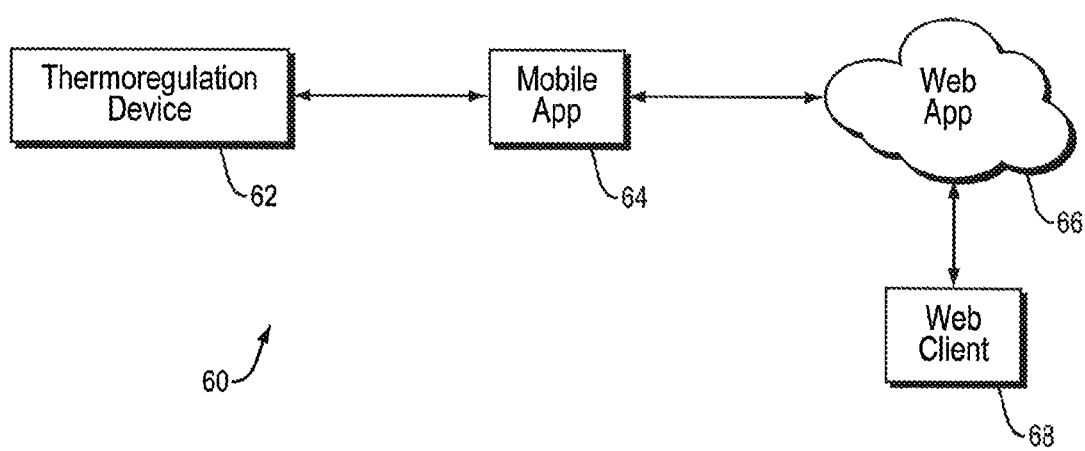
FIG. 6 is a schematic diagram of a system architecture for a wearable thermoregulation device.

FIG. 6 illustrates an exemplary system block diagram for a system 60 that uses thermoregulation device 62. Device 62 is wirelessly coupled (e.g., via a Bluetooth protocol) to mobile device (e.g., cell phone) that is running a mobile app 64. The mobile device communicates wirelessly (e.g., via WiFi) with web app 66, which itself can wirelessly communicate with web client 68 (which may allow data to be viewed in a web browser and/or may represent an administrator of system 60).

Figure 7A:
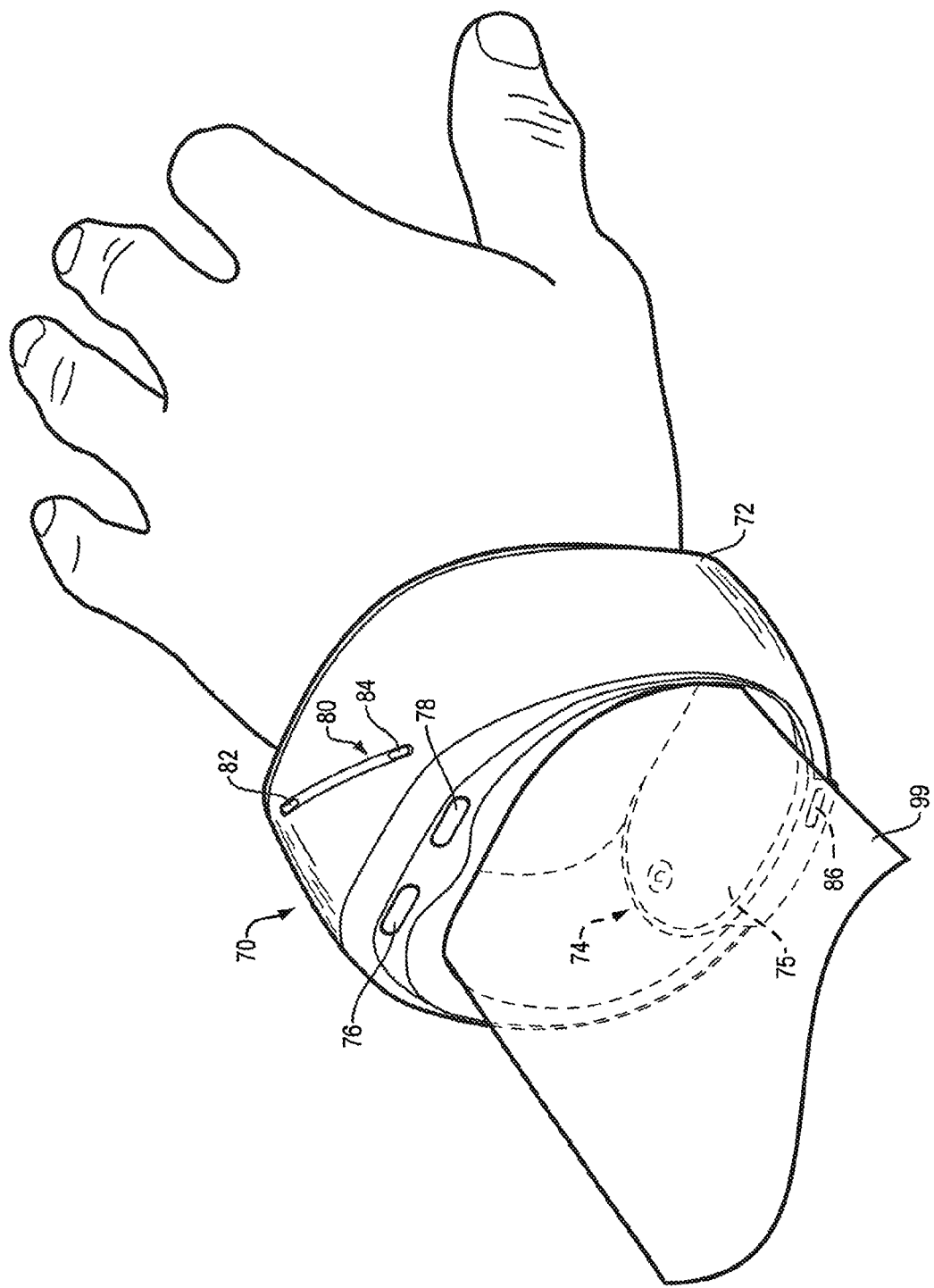
FIGS. 7A-7C illustrate a wearable thermoregulation device.
Figure 7B:
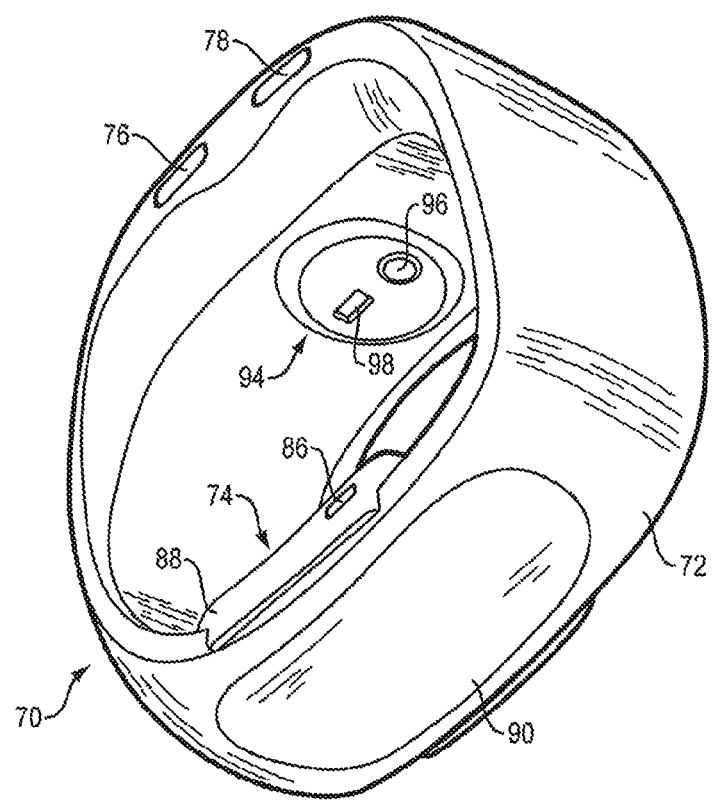
Figure 7C:
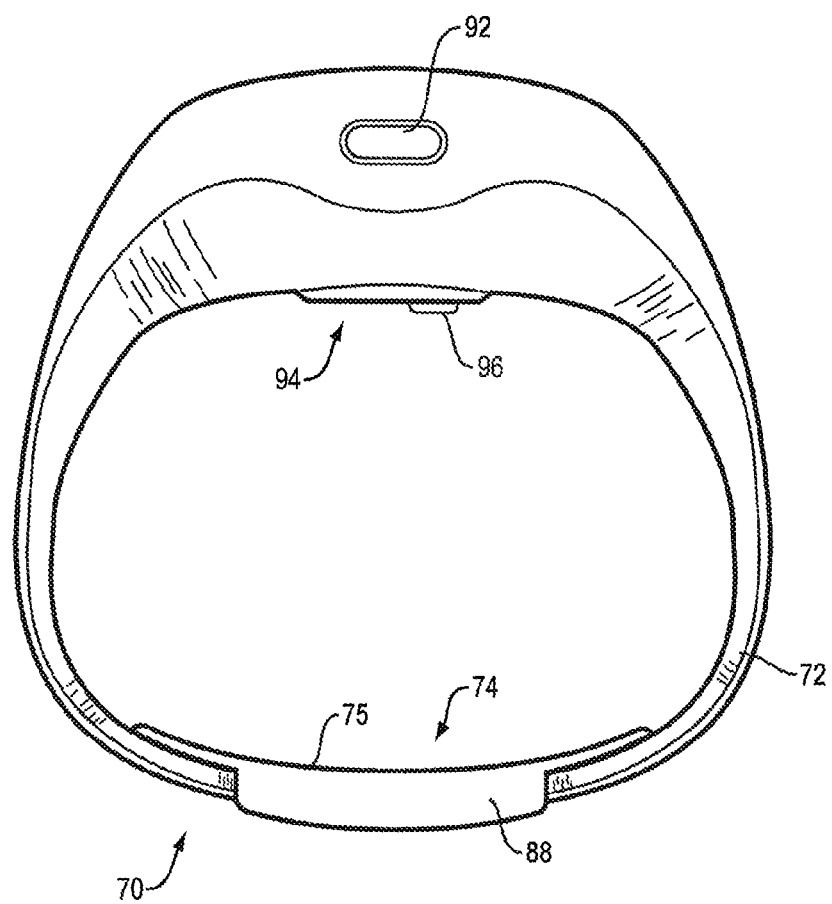

FIGS. 7A-7C illustrate one non-limiting example of a wrist-wearable thermoregulation device 70 being worn on user's arm 99. Device 70 includes band (carrier structure) 72 to which is fixed TEC module 74 that includes output cooling/heating stainless steel plate 75 on the skin side (where it rests against the bottom of the wrist/arm) and opposed heatsink 90 that is exposed to the air, to dissipate heat or cold. The heatsink can include radiator fins. Such radiator fins can be oriented parallel to the most common axis of motion of the device as it is worn, to improve airflow and efficiency. The most common axis of motion is the most typical way a body part moves. In the case of a wrist, that would be across the wrist as that's the way a wrist moves whenever the elbow is bent in anything other than a first pumping motion. Charge port 86 allows the device to be coupled to a battery charger. Side portion 88 helps to fix module 74 to band 72. User input buttons 76, 78, and 92 are on the top side for easy user access. Exemplary device status-indicating LED set 80 includes two different color LEDs 82 and 84. Top underside instrumentation module 94 includes pulse sensor 98 and skin temperature sensor 96, which protrudes slightly so that it makes good thermal contact with the skin and in some cases comprises a thin stainless-steel cap, with a thermistor inside that is coupled to the cap using a thermal paste.

Figure 8:
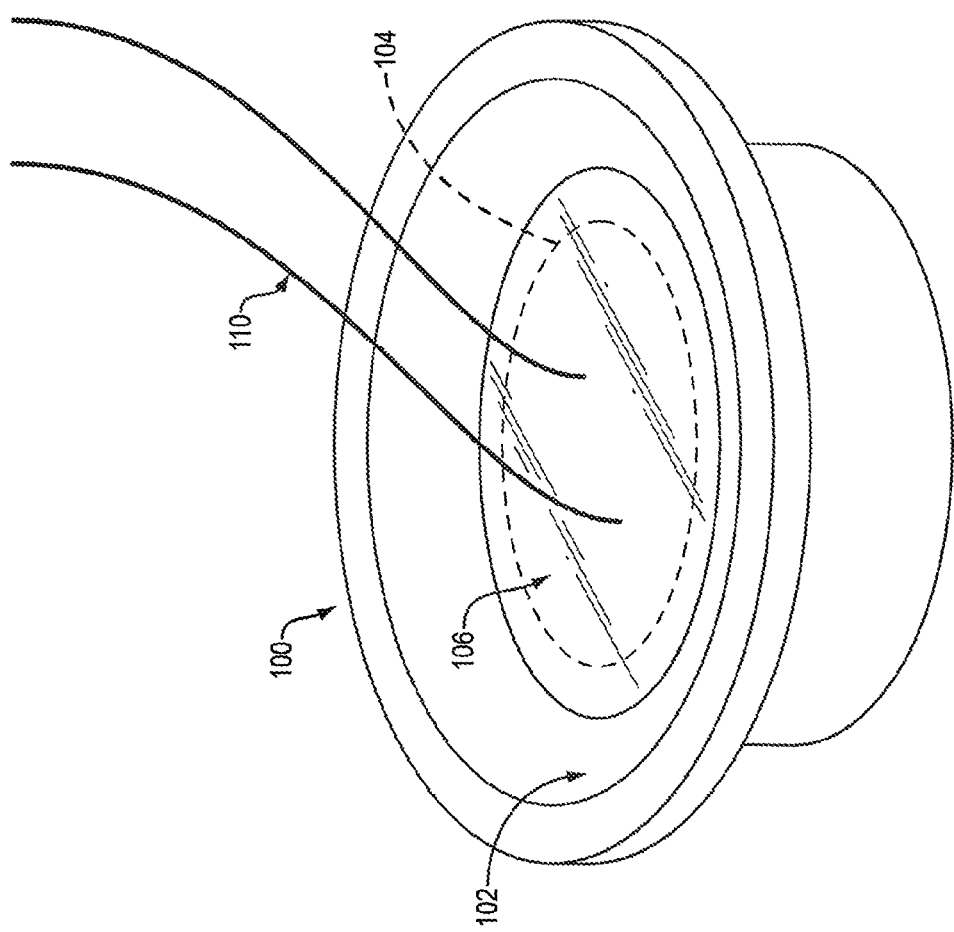
FIG. 8 illustrates a temperature sensor used to determine the skin temperature of a person wearing the wearable thermoregulation device.

FIG. 8 illustrates an exemplary skin temperature sensor 100 comprising stainless-steel bowl-shaped cap 102 in which is fitted a thermistor 104 that is not visible because it is embedded in thermal compound 106 that fills the cap and fills any space between the thermistor and the inside surface of cap 102 that is opposed to the outside surface of cap 102 that is configured to touch the user's skin. Wire set 110 feeds the thermistor output to processing circuitry, which includes the controller.

Following are further illustrative, non-limiting examples of control aspects for the thermoregulation device. In an example the inputs to the control algorithm can receive additional input from data collected outside of the device (e.g., by other users). This data can be used to modify the device function. An example would be that an elevated heart rate and restless night's sleep (as determined by the accelerometer) along with skin temperature could be used as inputs to identify a user pattern that would generate a profile to control the TEC for a cooling or heating event when certain criteria are met.

In some examples inputs to the control algorithm include one or more of: Date/Time, Temperature sensor—wrist, Temperature sensor—device, User weighting up (historical button presses for hot), User weighting down (historical button presses for cold), Number of concurrent button presses up concurrent to operation, Number of concurrent button presses down concurrent to operation, Heart rate, Physical activity status, Sp02 level, Blood pressure, Skin conductivity, User sleep status, Ambient temperature, % current temperature of TEC, and % duration of operation of TEC. Note that current temperature and duration of operation are both outputs of the device, and can be re-input in a typical neural net or other machine learning technique in order to add 'safety' dimensions to device operation. These inputs can be used in any combination, and other inputs can be used.

Following are illustrative, non-limiting examples of control algorithms. One is a simple input/output map where a given discrete input is matched to a given discrete output. Another is a more complex input/output map where button presses establish a user preference history to modify the desired output map for a given input. An even more complex map could be where button presses form a time series user preference for a given input to further modify the desired output with respect to duration or other functionality. In any of these the inputs can be provided to a third piece of technology for analysis and post processing to further refine the output map towards the user's preference; off-device machine learning would be a typical way to do this.

The examples herein are indicative of basic operations in a format that is easy to understand. The actual implementation of the device may be dependent on one or more inputs, including but not limited to those described herein. Other inputs can be added to further tailor the behavior of the device to the user's preferences and environment.

In an example of matching a discrete input to a discrete output, the TEC can be controlled to have a discrete number of cold and hot levels (i.e., TEC output temperatures), 1-5, where a negative level equals cooling. See Table 1 for a sample discrete matching of measured skin temperature vs. TEC level output.

TABLE 1

| Skin Temperature, ° F. (input) | TEC level (output) |
| --- | --- |
| <84 | 5 |
| 85 | 4 |
| 86 | 3 |
| 87 | 2 |
| 88 | 1 |
| 89 | 0 |
| 90 | 0 |
| 91 | 0 |

TABLE 1-continued

| Skin Temperature, ° F. (input) | TEC level (output) |
|---|---|
| 92 | −1 |
| 93 | −2 |
| 94 | −3 |
| 95 | −4 |
| >96 | −5 |

Table 2 is an example of how the control scheme in Table 1 could be altered based on user input (e.g., button pushes indicative of the user feeling too hot or too cold and pushing buttons to activate the TEC device to provide cold or heat). The user in this case has had several hot and cold flashes and the buttons that they pushed on the device have set the user preferences accordingly. We can see here that the user generally does not want the device at maximum output (level 5) for hot or cold, as well they seem to have indicated that they want cooling events to start earlier than the default in Table 1.

TABLE 2

| Skin Temperature, ° F. (input) | TEC level (output) |
|---|---|
| <84 | 4 |
| 85 | 2 |
| 86 | 1 |
| 87 | 0 |
| 88 | 0 |
| 89 | 0 |
| 90 | −1 |
| 91 | −1 |
| 92 | −3 |
| 93 | −4 |
| 94 | −4 |
| 95 | −4 |
| >96 | −4 |

Table 3 illustrates a simple device control scheme on the left side, with changes due to button pushes on the right side, with button pushes as a separate input. In Table 3, C=cold button (i.e., user feels cold), H=hot button (i.e., user feels hot).

TABLE 3

| Skin Temperature, ° F. (input) | TEC level (output) | Button Pushed, and Number of Pushes | Skin Temperature, ° F. (input) | TEC level (output) |
|---|---|---|---|---|
| <84 | 5 | C-1 | <84 | 4 |
| 85 | 4 | C-2 | 85 | 2 |
| 86 | 3 | C-2 | 86 | 1 |
| 87 | 2 | C-2 | 87 | 0 |
| 88 | 1 | C-1 | 88 | 0 |
| 89 | 0 | 0 | 89 | 0 |
| 90 | 0 | C-1 | 90 | −1 |
| 91 | 0 | C-1 | 91 | −1 |
| 92 | −1 | C-2 | 92 | −3 |
| 93 | −2 | C-2 | 93 | −4 |
| 94 | −3 | C-1 | 94 | −4 |
| 95 | −4 | 0 | 95 | −4 |
| >96 | −5 | H-1 | >96 | −4 |

Table 4 is a more complex reference implementation that involves time. The way that this would work is we know when the device moves up and down levels in heating based on the input temperature sensor. In the Table, there is a button press any time there is a change in either temperature or the duration of operation of the TEC. Outcomes in the Table are affected by the contextual cues and therefore there can be multiple paths to go from the left side of the Table to the right side. If there is a corresponding button press (up or down) close to when those levels change, rather than change the desired output at that temperature, we can set the desired length of time at the preceding temperature to +/−some time interval. Table 4 implies 30 seconds are added to the desired output. If a button press occurs further away from a level change, we change the output level and not the time. The user has changed both the temperature and the desired output time for various levels. We can see that they generally prefer longer periods of temperature output by the TEC.

Some implications for Table 4: Basically when the device is performing some operation and a button press comes in, there needs to be some logic associated with the amount of time since that operation began, and what the input was in order to make an intelligent decision. If for example the user pushes the down button three times in rapid succession, we probably want to ignore the second presses as the device output does not change instantly. We can however say more definitively that the device isn't doing what the user wants, and may want to give more weighting to changing output temperature rather than time for example.

TABLE 4

| Skin Temperature, ° F. (input) | TEC level (output) | Duration (sec.) | Skin Temperature, ° F. (input) | TEC level (output) | Duration (sec.) |
|---|---|---|---|---|---|
| <84 | 5 | 60 | <84 | 4 | 150 |
| 85 | 4 | 60 | 85 | 2 | 120 |
| 86 | 3 | 60 | 86 | 1 | 60 |
| 87 | 2 | 60 | 87 | 0 | nil |
| 88 | 1 | 60 | 88 | 0 | nil |
| 89 | 0 | nil | 89 | 0 | nil |
| 90 | 0 | nil | 90 | −1 | 90 |
| 91 | 0 | nil | 91 | −1 | 90 |
| 92 | −1 | 60 | 92 | −3 | 120 |
| 93 | −2 | 60 | 93 | −4 | 300 |
| 94 | −3 | 60 | 94 | −4 | 300 |
| 95 | −4 | 60 | 95 | −4 | 300 |
| >96 | −5 | 60 | >96 | −4 | 300 |

Having described above several aspects of at least one example, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A wearable thermoregulation device configured to be worn on the body of a user, comprising:
   a band that is configured to be worn on the user's arm or wrist;
   a thermoelectric device carried by the band and that is configured to controllably heat and cool a control surface that is configured to contact the user's skin on one of the bottom or top of the user's arm or wrist;
   a power source carried by the band and that is configured to provide power to operate the thermoelectric device and either heat or cool the control surface;
   a controller carried by the band;
   a skin temperature sensor carried by the band at a location circumferentially spaced from the control surface of the thermoelectric device such that it is thermally isolated from the control surface of the thermoelectric device so that it is not influenced by heat or cold from the control surface, wherein the skin temperature sensor is configured to be in direct contact with the skin of the user and is configured to be used to sense skin temperature over time;
a control surface temperature sensor carried by the band and that is configured to determine a temperature of the control surface, wherein the control surface temperature sensor is in communication with the controller;
a wireless communications module carried by the band and that is configured to wirelessly send signals from the controller, and wirelessly receive signals, to control the thermoelectric device;
wherein the skin temperature sensor is configured to be used by the controller to determine a skin temperature increase over time that indicates the onset of a hot-flash event;
wherein in response to the determination of a hot-flash event the controller causes the thermoelectric device to cool the control surface;
wherein the skin temperature sensor continues to monitor skin temperature without thermal influence by the control surface while the control surface is cooled; and
wherein the controller is further configured to cause the thermoelectric device to stop cooling the control surface based at least in part on skin temperature as determined by the skin temperature sensor.

2. The wearable thermoregulation device of claim 1, wherein the skin temperature sensor comprises a temperature sensor located proximate a metal surface that is configured to touch the user's skin.

3. The wearable thermoregulation device of claim 2, wherein the skin temperature sensor further comprises a thermally-conductive material between the temperature sensor and the metal surface.

4. The wearable thermoregulation device of claim 1, further comprising a heart rate sensor carried by the band such that it is configured to be in direct contact with the user's skin, wherein the heart rate sensor is in communication with the controller.

5. The wearable thermoregulation device of claim 1, further comprising a six-axis motion tracking device carried by the band, wherein the six-axis motion tracking device is in communication with the controller.

6. The wearable thermoregulation device of claim 1, wherein the controller comprises firmware that is configured to smooth temperature sensor data.

7. The wearable thermoregulation device of claim 1, wherein the controller comprises firmware that is configured to detect an upward inflection point in the sensed skin temperature over time.

8. The wearable thermoregulation device of claim 1, wherein the controller comprises firmware that is configured to sum temperature data from a plurality of separate temperature sensors.

9. The wearable thermoregulation device of claim 1, further comprising at least one user input device.

10. The wearable thermoregulation device of claim 9, wherein the controller is responsive to both the skin temperature sensor and the at least one user input device.

11. The wearable thermoregulation device of claim 10, wherein the controller is configured to control a cold level of the control surface based on both the sensed skin temperature and the at least one user input device.

12. The wearable thermoregulation device of claim 1, wherein inputs to the controller include at least one of: Date/Time, Temperature sensor—wrist, Temperature sensor—device, User weighting up, User weighting down, Number of concurrent button presses up concurrent to operation, Number of concurrent button presses down concurrent to operation, Heart rate, Physical activity status, Sp02 level, Blood pressure, Skin conductivity, User sleep status, and Ambient temperature.

13. The wearable thermoregulation device of claim 1, wherein the device creates outputs that are input in a typical neural net or other machine learning technique in order to add safety dimensions to device operation.

14. The wearable thermoregulation device of claim 13, wherein the outputs comprise at least one of % current temperature of TEC, and % duration of operation of TEC.

15. The wearable thermoregulation device of claim 1, wherein the controller is configured to implement a control algorithm.

16. The wearable thermoregulation device of claim 15, wherein the control algorithm is selected from a group of control algorithms consisting of a simple input/output map where a given discrete input is matched to a given discrete output, a more complex input/output map where button presses establish a user preference history to modify the desired output map for a given input, an even more complex input/output map where button presses form a time series user preference for a given input to further modify the desired output with respect to duration or other functionality.

17. The wearable thermoregulation device of claim 15, wherein the control algorithm is responsive to multiple inputs comprising at least biometric inputs, direct inputs from a user, implicit inputs, and contextual inputs, in order to control the thermoelectric device in accordance with the user's desires.

\* \* \* \* \*